United States Patent [19]

Tezuka et al.

[11] Patent Number: 5,569,287
[45] Date of Patent: Oct. 29, 1996

[54] MEANS FOR COLLECTING AND SPOTTING SMALL AMOUNT OF BLOOD

[75] Inventors: Shigeru Tezuka; Hikaru Tsuruta; Teruaki Koizumi; Masao Kitajima, all of Saitama, Japan

[73] Assignee: Fuji Photo Film Co., Ltd., Kanagawa, Japan

[21] Appl. No.: 353,108

[22] Filed: Dec. 9, 1994

[30] Foreign Application Priority Data

Dec. 9, 1993 [JP] Japan .................................. 5-341510
Apr. 11, 1994 [JP] Japan .................................. 6-098130

[51] Int. Cl.⁶ .................................................. A61B 17/14
[52] U.S. Cl. .................................................. 606/182
[58] Field of Search ........................... 128/770; 606/167, 606/181, 182

[56] References Cited

U.S. PATENT DOCUMENTS

| | | | |
|---|---|---|---|
| 4,553,541 | 11/1985 | Burns | 606/182 |
| 5,026,388 | 6/1991 | Ingalz | 606/182 |
| 5,318,584 | 6/1994 | Large et al. | 606/182 |
| 5,356,420 | 10/1994 | Czernecki et al. | 606/181 |

*Primary Examiner*—Max Hindenberg
*Attorney, Agent, or Firm*—McAulay Fisher Nissen Goldberg & Kiel, LLP

[57] ABSTRACT

A means for collecting and spotting a small amount of blood which comprises a cylinder, a piston, and a puncturing tip, wherein: the piston is inserted airtightly into one end of the cylinder; the puncturing tip is airtightly and exchangeably fitted onto another end of the cylinder; the puncturing tip comprises a blood conduit and a needle suspended by a spring within the blood conduit; the blood conduit has a volume which is equal to a volume of blood to be spotted to analytical means; and the needle is arranged to be pushed out from the puncturing tip by descent of the piston and then return back by ascent of the piston.

3 Claims, 8 Drawing Sheets

5,569,287

MEANS FOR COLLECTING AND SPOTTING SMALL AMOUNT OF BLOOD

FIELD OF THE INVENTION

This invention relates to means for collecting and spotting a small amount of blood.

BACKGROUND OF THE INVENTION

In the medical and health examinations, the blood is generally tested. For performing the blood test, a small but certain amount of blood is required. Generally, the blood is taken by an expert such as a medical doctor or a nurse through vein. In some cases, several drops of blood are taken by slightly injuring a finger tip or an earlobe.

As means for testing the blood in clinical tests, there are known multi-layered analytical elements which contain chemical reagents, biochemical reagents, or immunological reagents. In the clinical tests using the multi-layered analytical elements (possibly, in the form of an analytical slide), a small but predetermined amount of the blood should be spotted onto the analytical element for causing a color development in the element. The developed color is then measured at a predetermined wavelength to quantitatively determine the analyte in the blood.

The procedure for collecting the blood is also performed by a patient per se, for checking blood sugar level or cholesterol level by himself. Particularly, in the case of diabetic, the blood sugar level ought to be checked frequently (for instance, several times a day), though each check procedure requires only a small amount of the blood. Generally, the blood is taken at a finger tip, because a great number of blood vessels are gathered at the finger tip. However, the blood collection at the finger tip sometimes causes acute pain, because a great number of nerves are also gathered at the finger tip. The blood collection at the finger tip is also sometimes troublesome, because the finger tip is frequently used for daily works. For these reasons, the blood collection at other portions is sometimes required.

Therefore, it is required to provide a blood collecting and spotting means which is employable for taking a small amount of blood and spotting a predetermined amount of blood onto an analytical means with little pain and no complicated procedures.

Japanese Patent Provisional Publications No. 62-38140, No. H-1-185245, and No. H-5-95938 describe means for collecting a small amount of blood from a human body with simple operation. These means, however, are not designed for spotting a predetermined amount of the collected blood sample onto an analytical means.

SUMMARY OF THE INVENTION

The present invention has an object to provide a blood collecting and spotting means which is employable for taking a small amount of blood and spotting a predetermined amount of blood onto an analytical means with little pain and no complicated procedures.

The invention also has an object to provide a blood collecting and spotting means which is repeatedly employable with replacement of a needle tip.

The present invention resides in a means for collecting and spotting a small amount of blood which comprises a cylinder, a piston, and a puncturing tip, wherein:

the piston is inserted airtightly into the upper end of the cylinder;

the puncturing tip is airtightly and exchangeably fitted onto the lower end of the cylinder;

the puncturing tip comprises a blood conduit and a needle suspended by a spring within the blood conduit;

the blood conduit has a volume which is equal to a volume of blood to be spotted to analytical means; and the needle is arranged to be pushed out from the puncturing tip by descent of the piston and then return back by ascent of the piston.

DETAILED DESCRIPTION OF THE INVENTION

The present invention is described in more detail by referring to the attached drawings.

Figure 1:
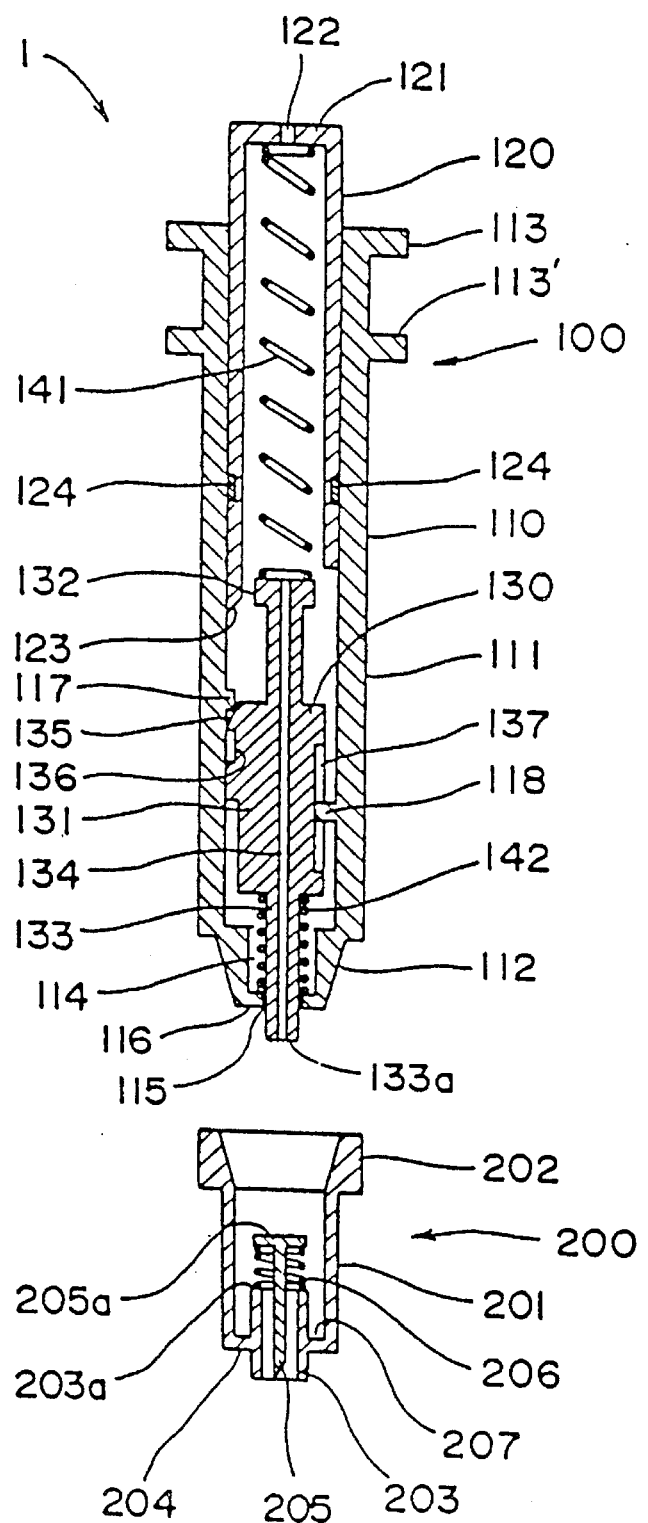
FIG. 1 illustrates an example of the means for collecting and spotting a small amount of blood according to the invention, by separating the cylinder portion and puncturing tip.

In FIG. 1, an example of the blood collecting and spotting means 1 comprises a main body 100 and a puncturing tip 200.

The main body 100 is composed of a cylinder 110, a piston 120, and a sliding means 130. The cylinder 110 has a tapered cylinder portion 112 at the lower end of the cylindrical portion 111 and two flanges 113, 113' at the upper end. The piston 120 is inserted into the cylinder 110 under such condition that the piston 120 is able to descend and ascend within the cylinder 110.

The puncturing tip 200 has a cylindrical body 201 whose opened upper end 202 is so tapered that the tip is airtightly and exchangeably fitted to the tapered cylinder portion 112 of the cylinder 110. The puncturing tip 200 further has a lower portion 204 which is provided with a blood conduit 203 (which also serves to quantitatively receive the blood to be spotted) and an excess blood receiver 207. Within the blood conduit, a needle 205 is suspended by a coil spring 206 under engagement between the upper end 203a of the blood conduit 203 and the upper end 205a of the needle 205.

When the puncturing tip 200 is fitted to the main body 100, the lower end of the needle 205 is encased in the blood conduit 203. However, the needle 205 is pushed down (or protruded) from the lower end of the blood conduit 203 by descending action of the sliding means. Under the condition, the needle 205 is protruded by a length of 1 to 2 mm from the lower end of the blood conduit 203.

In the tapered cylinder portion 112, a space 114 having a diameter smaller than the diameter of that of the cylindrical portion is formed. The lower end of the tapered cylinder portion 112 is composed of a further smaller hole 115 and a bottom portion 116. The outer surface of the tapered cylinder portion 112 is so processed as to be airtightly and exchangeably inserted into the upper end 202 of the puncturing tip 200. The puncturing tip 200 is attached to the tapered cylinder portion 112 by friction. However, the puncturing tip can be screwed into the cylinder 110. Otherwise, other connecting means can be employed for keeping the cylinder and the puncturing tip from separation.

The piston 120 has a bottom 121 at the upper end, and the bottom 121 has a hole 122. The piston 120 has a wall whose lower end 123 is shaped in the form of wedge. On the outer surface of the piston 120, a sealing means 124 is provided so as to seal the space between the inner surface of the cylinder 110 and the outer surface of the piston 120.

The sliding means 130 is composed of a cylindrical body 131, a spring supporting means 132, and a pushing means 133. The sliding means 130 has a through-hole 134 which allows passage of air therethrough. A portion 135 of the upper part of the cylindrical body 131 is cut off. Just under the cut-off portion 135, an indented portion 136 is formed. The cylinder 110 has a protruded portion 117 on the inner surface of its wall in the portion above the cut-off portion 135 of the sliding means 130. When the sliding means 130 is pushed up (details will be described hereinafter) to engage the indented portion 136 with the protruded portion 117, the lower end 133a of the pushing means 133 is located on the same level as that of the lower end of the tapered cylinder portion 112. Further, on the outer surface of the cylindrical body 131, a vertically extended groove 137 is formed. The groove 137 is engaged with a projecting portion 118 of the cylinder 110 so that the sliding means 130 can do up-and-down movement only.

Between the upper bottom 121 of the piston 120 and the top of the spring supporting means 132, a spring 141 is provided. Further, between the lower end of the cylindrical body 131 and the bottom portion 116 of the tapered cylinder portion 112, a spring 142 is provided. The sliding means 130 is pushed up by the spring 132 to keep the sliding means 130 under such condition that the upper end of the cylindrical body 131 is positioned in contact with the lower surface of the protruded portion 117.

Each of the cylinder, piston and sliding means can be preferably made of hard plastic material such as polystyrene, high density polyethylene, polypropylene, poly(vinyl chloride), polyacrylate resin or polycarbonate. The sealing means can be in the form of a ring and can be made of rubber or soft plastic material such as soft poly(vinyl chloride) or low density polyethylene. Each of the springs 141, 142 preferably is a coil spring.

The puncturing tip is preferably made of plastic material in one unit (except for the needle). The plastic material preferably is transparent or semi-transparent so as to be easily check the blood received in the puncturing tip. The plastic material can be hydrophilic or hydrophobic. However, the puncturing tip made of hydrophilic plastic material is favorably employed because the blood can enter easily and smoothly into the blood conduit. Examples of the hydrophilic plastic material include polyamide and ethylene-carboxylate copolymer, both of which are inherently hydrophilic. However, a hydrophobic plastic material which is made hydrophilic by compounding a hydrophilic plasticizer such as glycerol, ethylene glycol, polyethylene glycol, or glycerol fatty acid ester (e.g., glycerol laurate or glycerol stearate) also can be employed.

Otherwise, the puncturing tip is once made of hydrophobic plastic material and coated with a hydrophilic material at the inner surface of the blood conduit. Examples of the hydrophilic material include surface active agents (particularly, nonionic surfactants), hydrophilic polymer, and water-soluble organic compounds (e.g., glycerol ester, ethylene glycol, amino acid, and sugar).

The spring 206 can be any form of spring means. A coil spring or leaf spring is preferred.

The procedures for collecting the blood by the use of the blood collecting and spotting means 1 of FIG. 1 according to the invention are described below by referring to FIGS. 2 to 5 in the drawings.

Figure 2:
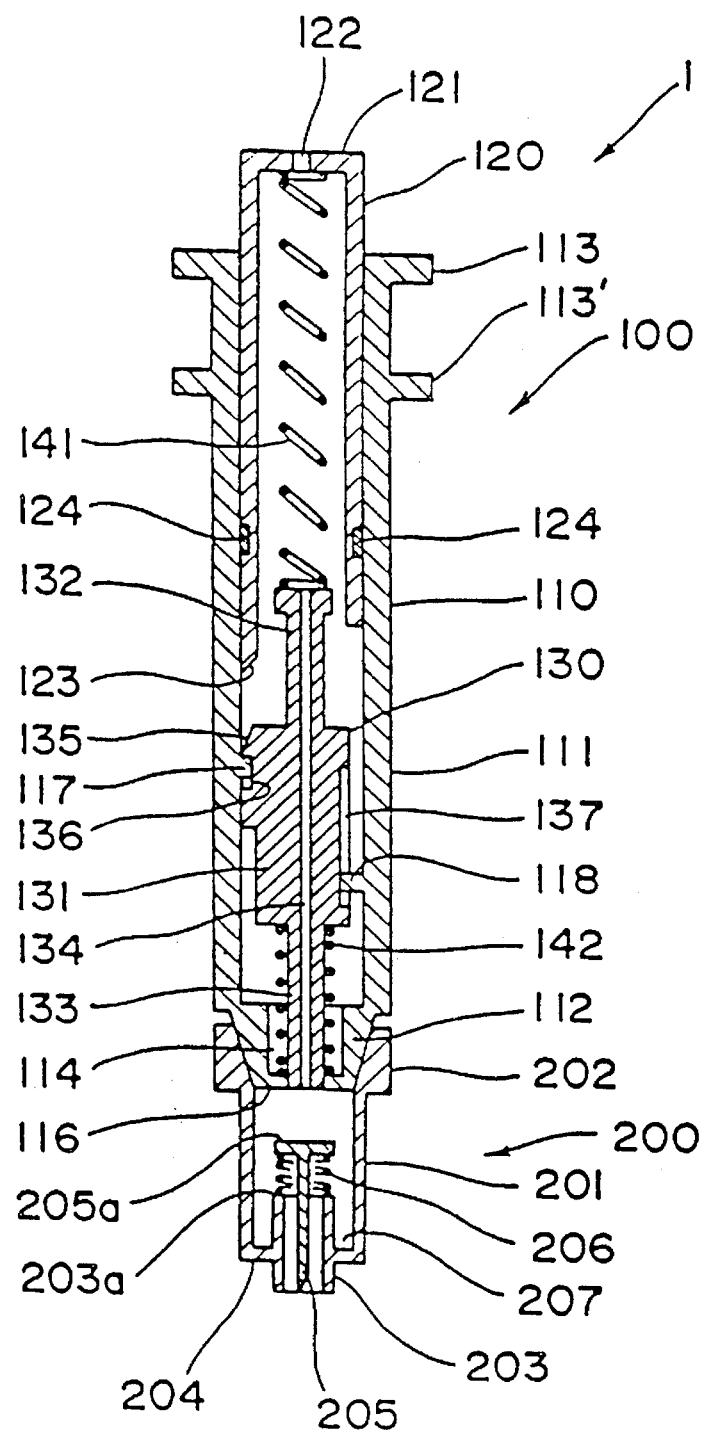
FIG. 2 illustrates the blood collecting and spotting means of FIG. 1 under the condition that the sliding means is pushed in and fixed and the puncturing tip is fitted to the cylinder.
Figure 3:
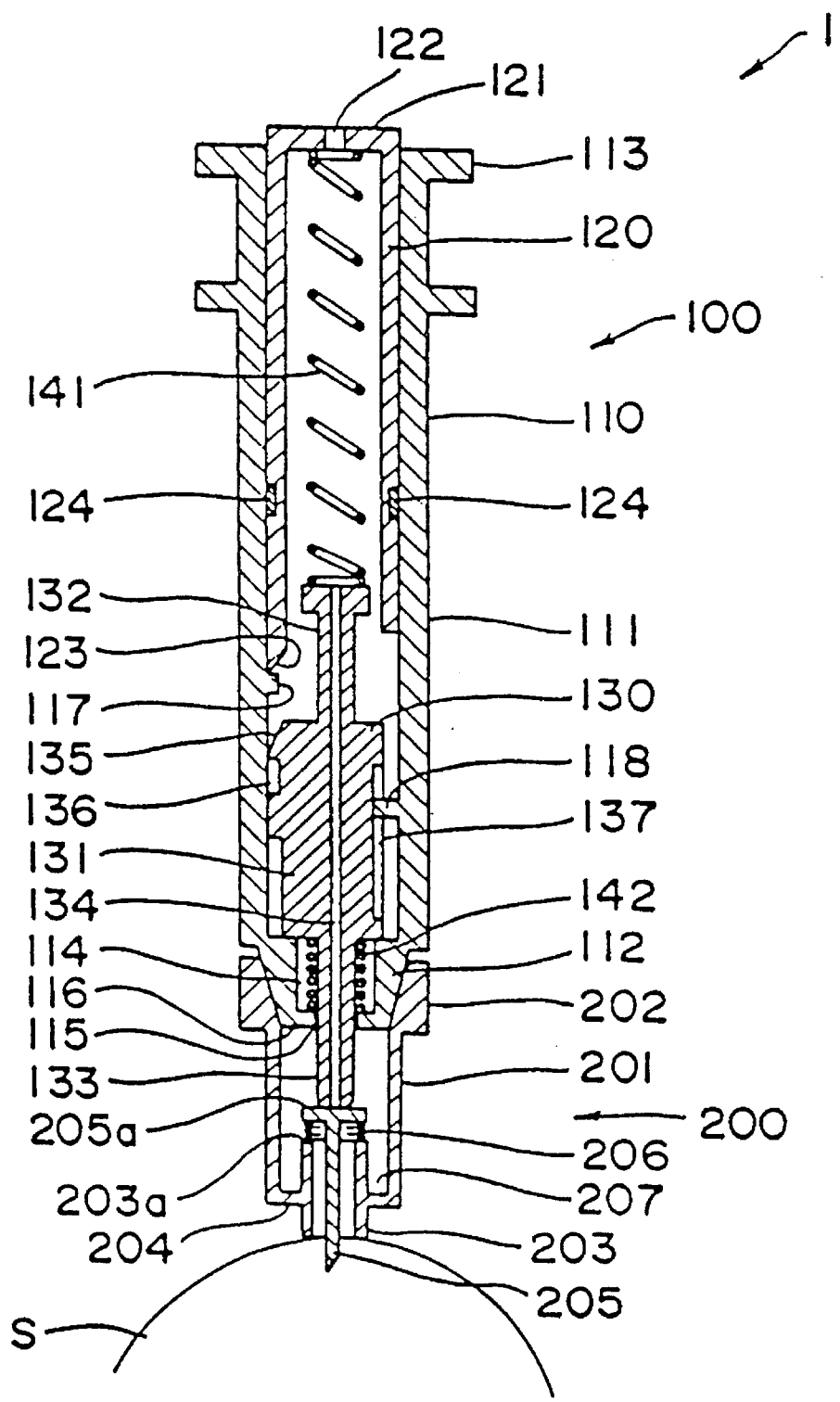
FIG. 3 illustrates the blood collecting and spotting means of FIG. 2 under the condition that the piston is pushed down, the sliding means is slide down and then the needle is pushed down to be inserted into a part of human body through skin.

First, the pushing means 133 protruding from the tapered cylinder portion 112 of the main body at its lower end 133a is pushed up by a finger so that the cut-off upper end of the cylindrical body 131 of the sliding means 130 can be disengaged with the protruded portion 117 and can move upward to engage the indented portion 136 with the protruded portion 117, as is illustrated in FIG. 2. Thereafter, the puncturing tip 200 is connected to the cylinder 110 by inserting the tapered cylinder portion 112 into the opened upper portion 202 airtightly. FIG. 2 shows the condition in that the puncturing tip 200 is connected airtightly to the cylinder 110. The numbers given in FIG. 2 indicate the same elements and portions as indicated in FIG. 1.

For collecting the blood, the lower end of the blood conduit 203 of the puncturing tip 200 is applied to a skin (S) of a human body, and the piston 120 is pushed down by pressing the upper end of the piston 120 by a finger (preferably, without closing the hole 122; other fingers are placed between the pair of flanges 113, 113'). Initially, the sliding means 130 is not moved because of the engagement with the protruded portion 117, and the spring 141 is contracted. When the piston 120 is further descended, the wedge end 123 is inserted between the inner surface of the cylinder 110 and the cut-off upper end of the sliding means 130 to remove the engagement. By the disengagement, the sliding means 130 is instantly pushed down by the expanding action of the contracted spring 141. Then, the pushing means 133 quickly protrudes from the tapered cylinder portion 112. The lower end of the pushing means 133 then pushes the upper end 205a of the needle 205 down, and the needle 205 protrudes slightly from the lower end of the puncturing tip 200 to enter into the skin. By this action, the springs 142, 206 are contracted.

Figure 4:
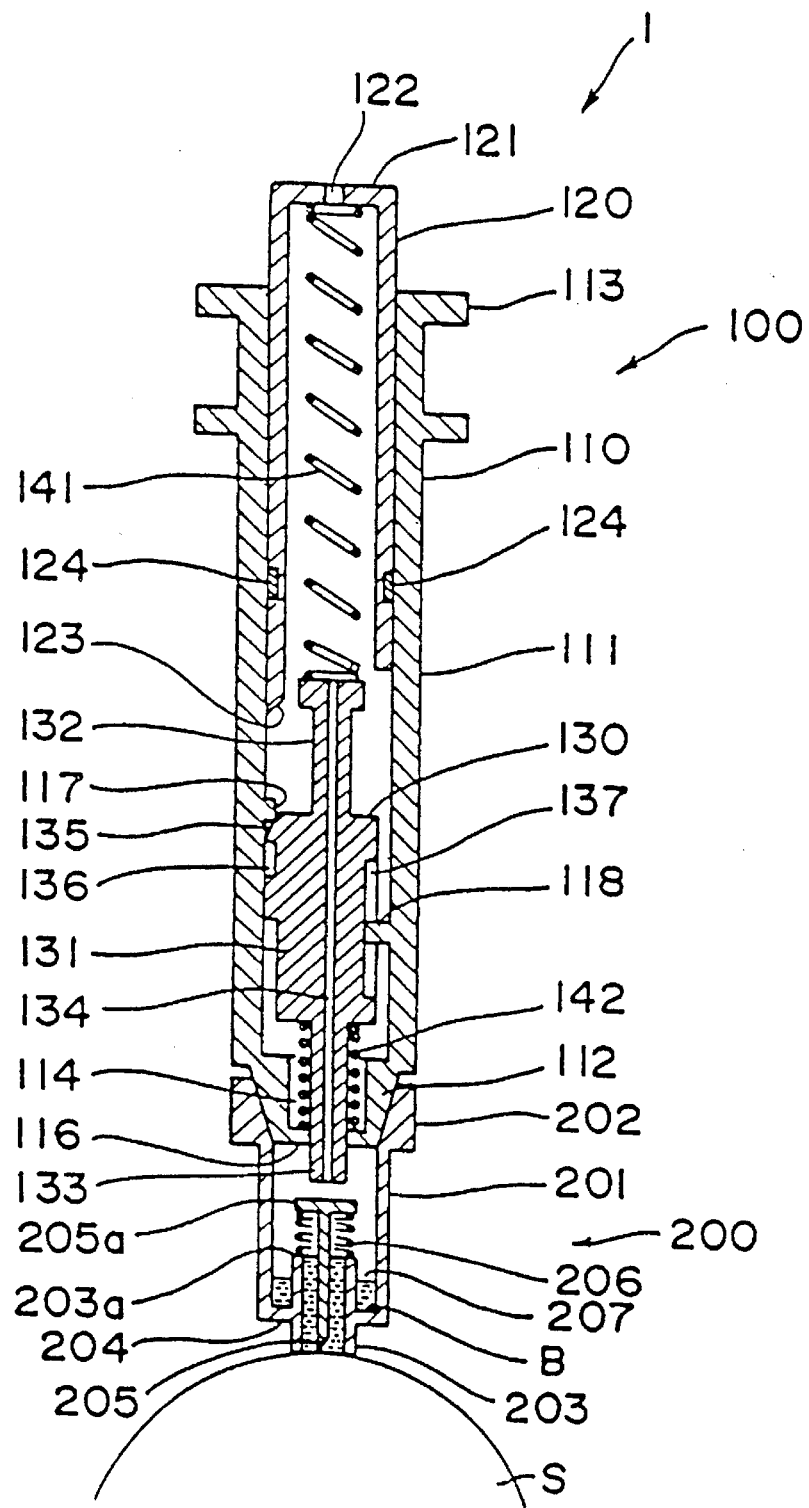
FIG. 4 illustrates the blood collecting and spotting means of FIG. 3 under the condition that the piston is returned to the original position, the sliding means is slide up, the needle is pushed up by the action of the spring, and then blood is taken out to fill up the blood conduit. An excess of the taken blood is received in a blood receiver of the puncturing tip.

After the needle 205 enters into the skin, the pushing means 133 is ascended by action of the contracted spring 142 to the position where the cut-off portion 135 of the sliding means is brought into contact with the protruded portion 117 of the cylinder. The spring 141 is then contracted. The needle 205 is also ascended by action of the contacted spring 206, for instance, 5 to 30 seconds after the insertion into the skin. In the course of the ascent of the needle 205, the blood oozes through the hole formed by the insertion of the needle. Then, the pressure of the finger applied to the top of the piston 120 is slowly reduced, at this time, with closing the hole 122. By the reduction of the pressure, the piston 120 is slowly ascended by action of the contracted spring 141. By the ascent of the piston 120, the pressure inside the cylinder 110 and puncturing tip 200 is reduced. As a result, the blood is introduced into the blood conduit 203. An excessive blood is received into the receiver 204. This condition is illustrated in FIG. 4.

Subsequently, the hole 122 of the piston is opened so that the pressure inside the cylinder 110 and puncturing tip 200 is returned to an atmospheric pressure. At the same time, the blood collecting and spotting means is removed from the skin. By the action of surface tension, the blood in the blood conduit 203 is kept without flowing down.

Figure 5:
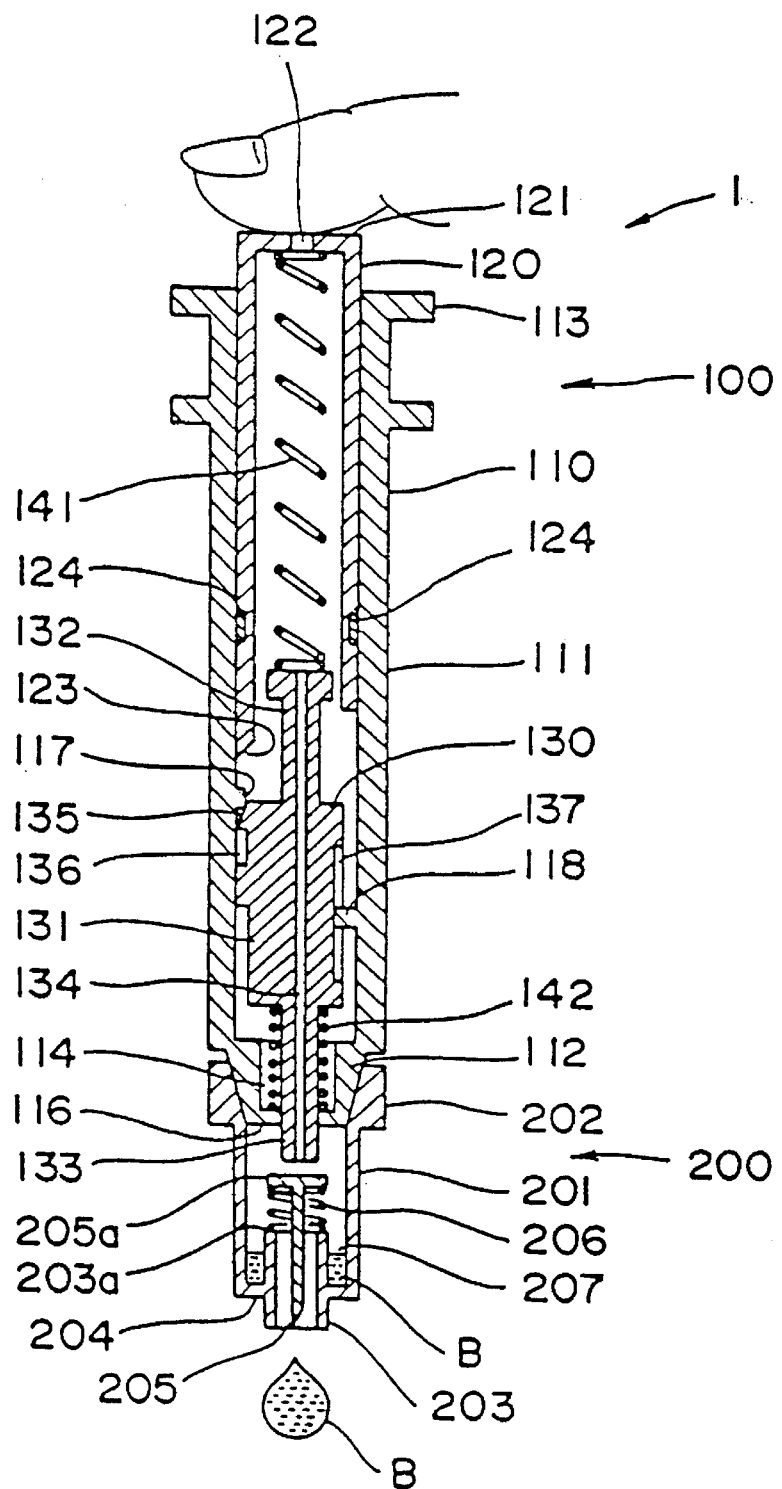
FIG. 5 illustrates the blood collecting and spotting means of FIG. 4 under the condition that the piston is again pushed down, the sliding means is slide down, and then a blood is pushed down to be spotted onto an analytical means (not shown).

The blood collecting and spotting means is then moved onto an analytical means, and the piston 120 is pushed down with closing the hole 122 by the finger to push the blood out of the blood conduit 203. The blood in the receiver 204 is not pushed out by this procedure. FIG. 5 shows this spotting procedure. If the analytical means is made of blood absorbable material such as paper sheet, cloth, or porous sheet, the blood in the blood conduit automatically flows out when the lower end of the blood conduit is brought into contact with the analytical means, without applying the pressure on the piston.

Accordingly, the volume of blood to be applied to the analytical means is automatically made equivalent to the inner volume of the blood conduit (after reduction of the volume of the needle). The volume of blood is kept at almost the same level in every blood collecting and spotting procedure, so long as the puncturing tip of the same size is employed in every procedure.

The needle and the blood conduit can be treated with an anticoagulant such as heparin or EDTA prior to initiating the blood collecting and spotting procedure, so that coagulation of the collected blood can be prevented.

After the blood collecting and spotting procedure is complete, the puncturing tip 200 is removed and disposed. Since the main body 100 having the cylinder, piston and pushing means is completely kept from the blood in the procedure, the main body 100 can be repeatedly employed by attaching a fresh puncturing tip.

The volume inside of the blood conduit 203 is optionally adjusted, generally, to a volume less than 100 μL, preferably in the range of 5 to 50 μL, more preferably in the range of 5 to 30 μL.

The hole 122 of the piston 120 can be omitted. In this structure, the volume of the blood introduced into the blood conduit can be adjusted by controlling the movement of the piston.

Figure 7:
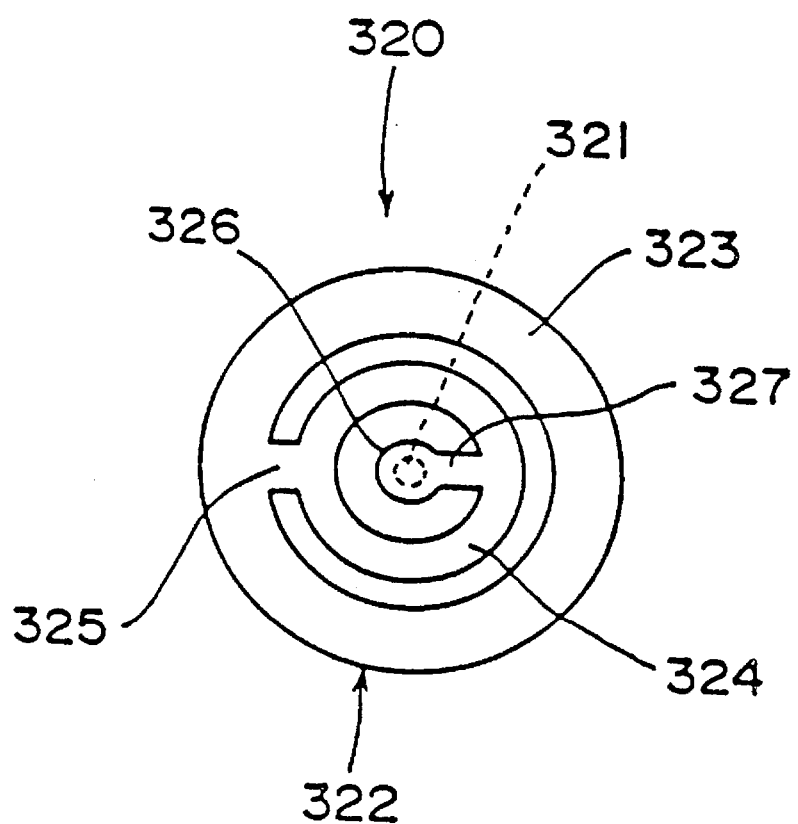
FIG. 7 illustrates a top view of the spring means for suspending the needle shown in FIG. 6.
Figure 8:
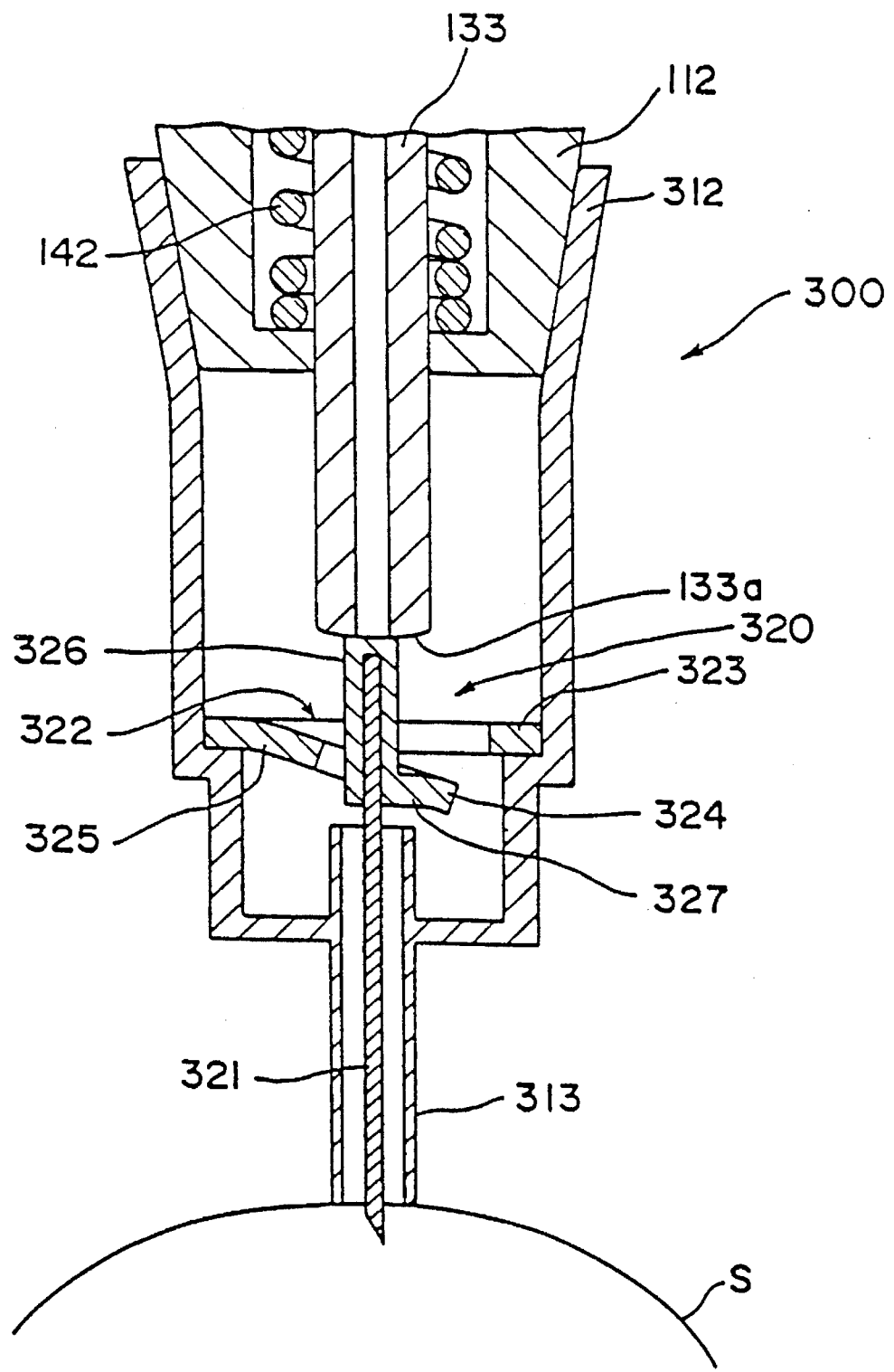
FIG. 8 illustrates a lower portion of the blood collecting and spotting means of FIG. 6 under the condition that the needle is inserted into a part of human body.

Further, one of other structures of the puncturing tip according to the invention is described below, by referring to FIGS. 6 to 8 in the attached drawings.

Figure 6:
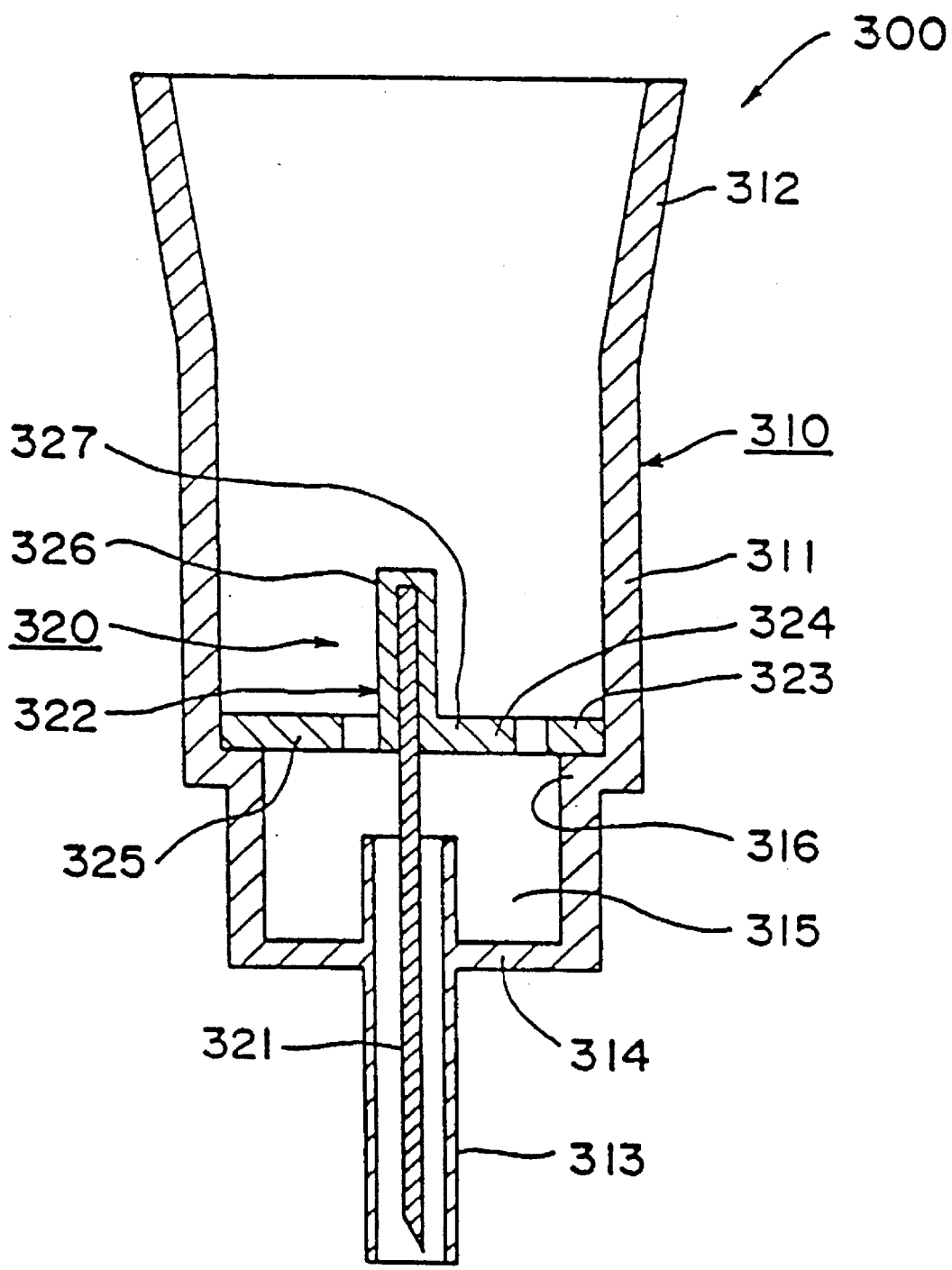
FIG. 6 illustrates another example of the puncturing tip to be attached to the blood collecting and spotting means of the invention.

In FIG. 6, a puncturing tip 300 comprises a housing 310 and a needle portion 320. The housing 310 is has a cylindrical body 311 whose upper end portion 312 is formed to be airtightly and exchangeably attached to the tapered cylinder portion 112 of the cylinder 110 and whose lower end has a blood conduit 313, a bottom plate 314, and an excessive blood receiver 315. The cylindrical body 311 further has a shelf 316 on its inner surface to fix thereon a needle supporting means 322 in the form of a disk (see FIG. 7).

The needle portion 320 comprises a needle 321 and a needle supporting means 322. The needle supporting means 322 comprises an outer ring 323 and an inner ring 324 which are connected via a flexible connecting portion 325 with each other. At the center of the needle supporting means 322, a cylindrical needle holder 326 is connected with the inner ring 324 with a flexible connecting portion 327. The combination of the flexible connecting portions 325, 327 functions as leaf spring to ensure the up-and-down movement of the needle 321.

The housing 310 is preferably formed in one unit, using hard plastic material. The needle supporting means 322 also is preferably formed in one unit which includes the outer ring 323, inner ring 324, connecting portions 325, 327, and cylindrical needle holder 326. The united needle supporting means is preferably made of polyethylene, polypropylene, acrylate polymer, or other plastic material. The needle 321 can be made of metal or plastic material. The plastic needle can be formed in one unit with the needle supporting means 322, for instance, by injection molding.

The procedures for collecting and spotting the blood using the puncturing tip 300 which is attached to the main body 100 are described below.

As is described before, initially the pushing means 133 is pushed into the cylinder 110, and the puncturing tip 300 is attached airtightly to the tapered cylinder portion 112.

In the blood collecting procedures, the piston is initially pushed down in the same manner as described hereinbefore. Then, the needle 321 is quickly pushed down to insert into a human body through a skin (S). In the puncturing tip 300, the needle supporting means 322, particularly, the combination of the flexible connecting portions 325, 327 functions as leaf spring in the same manner as the coil spring 206. Accordingly, the same procedures as those for the blood collecting and spotting means of FIGS. 1 to 5 can be done using the blood collecting and spotting means which is formed of the main body 100 and the puncturing tip 300 to collect the blood and spot a predetermined volume of the blood onto an analytical means with simple operations.

We claim:

1. An apparatus for collecting and delivering a small amount of blood which comprises a cylinder, a piston, and a puncturing tip, wherein the piston is inserted airtightly into the upper end of the cylinder;

the puncturing tip is airtightly and exchangeably fitted onto the lower end of the cylinder;

the puncturing tip comprises a blood conduit and a needle suspended by a spring within the blood conduit;

the blood conduit has a volume which is equal to a volume of blood to be delivered; and the needle is arranged to be pushed out from the puncturing tip by descent of the piston and then returned back by ascent of the piston, wherein the cylinder contains in its lower end, a sliding means having a through-hole therein, the top the sliding means being connected with the piston via a spring, the lower end of the sliding means protruding from the lower end of the cylinder, the lower end of the sliding means being able to be so pushed into the cylinder that the sliding means is fixed in a predetermined position under engagement with the inner surface of the cylinder and being able to be pushed down rapidly by breakage of the engagement which is caused by the descent of the piston.

2. The means as defined in claim 1, wherein the puncturing tip has a receiver for receiving an excess amount of the collected blood.

3. The apparatus of claim 1, wherein the needle is suspended within the blood conduit by means of a leaf spring of plastic material.

\* \* \* \* \*